(12) United States Patent
Hunter et al.

(10) Patent No.: US 8,938,046 B2
(45) Date of Patent: Jan. 20, 2015

(54) SYSTEM AND METHOD FOR UNDERWATER RADIOGRAPHY

(75) Inventors: James Hunter, Los Alamos, NM (US);
Danny Lee Keck, Katy, TX (US); James Rae Sims, Jr., Los Alamos, NM (US);
Scott Avery Watson, Los Alamos, NM (US)

(73) Assignee: BP Corporation North America Inc., Houston, TX (US)

( * ) Notice: Subject to any disclaimer, the term of this patent is extended or adjusted under 35 U.S.C. 154(b) by 15 days.

(21) Appl. No.: 13/458,260

(22) Filed: Apr. 27, 2012

(65) Prior Publication Data

US 2012/0275566 A1  Nov. 1, 2012

Related U.S. Application Data

(60) Provisional application No. 61/480,817, filed on Apr. 29, 2011.

(51) Int. Cl.
| | | |
|---|---|---|
| *G01N 23/04* | (2006.01) | |
| *G03B 42/02* | (2006.01) | |
| *G03B 42/04* | (2006.01) | |

(52) U.S. Cl.
CPC .............. *G01N 23/04* (2013.01); *G03B 42/028* (2013.01); *G01N 2223/646* (2013.01); *G01N 2223/407* (2013.01); *G01N 2223/631* (2013.01); *G03B 42/04* (2013.01)
USPC ............. 378/62; 378/181; 378/182; 378/197; 378/198

(58) Field of Classification Search
CPC ...... G01N 23/04; G03B 42/025; G03B 42/02; G03B 42/04; A61B 6/4283; A61B 6/4458; A61B 6/4405; H05G 1/02

USPC .......... 378/62, 167, 181, 182, 189, 193, 197, 378/198

See application file for complete search history.

(56) References Cited

U.S. PATENT DOCUMENTS

| | | | |
|---|---|---|---|
| 2,719,926 A | | 8/1952 | Procter et al. |
| 3,124,689 A | | 3/1964 | Shure |
| 3,445,655 A | | 5/1969 | Curry |
| 3,673,407 A | | 6/1972 | Wiswell, Jr. |
| 3,891,845 A | * | 6/1975 | English ........................ 378/58 |
| 3,993,906 A | | 11/1976 | English |
| 4,066,899 A | | 1/1978 | Gaspar et al. |
| 4,521,904 A | | 6/1985 | Takano |
| 5,960,058 A | * | 9/1999 | Baba et al. .................. 378/98.4 |

FOREIGN PATENT DOCUMENTS

EP   0120 565   1/1984

* cited by examiner

*Primary Examiner* — Jurie Yun
(74) *Attorney, Agent, or Firm* — Jayne C. Piana

(57) ABSTRACT

A system for subsea imaging comprises a first plate having an inner surface, an outer surface, and a cavity formed in the inner surface. In addition, the system comprises a phosphor imaging plate disposed in the cavity. Further, the system comprises a second plate having an inner surface facing the inner surface of the first plate and an outer surface facing away from the outer surface of the first plate. Still further, the system comprises a seal member disposed between the inner surface of the first plate and the inner surface of the second plate. The seal member extends around the perimeter of the cavity and is configured to seal the phosphor imaging plate and the cavity from intrusion water.

25 Claims, 10 Drawing Sheets

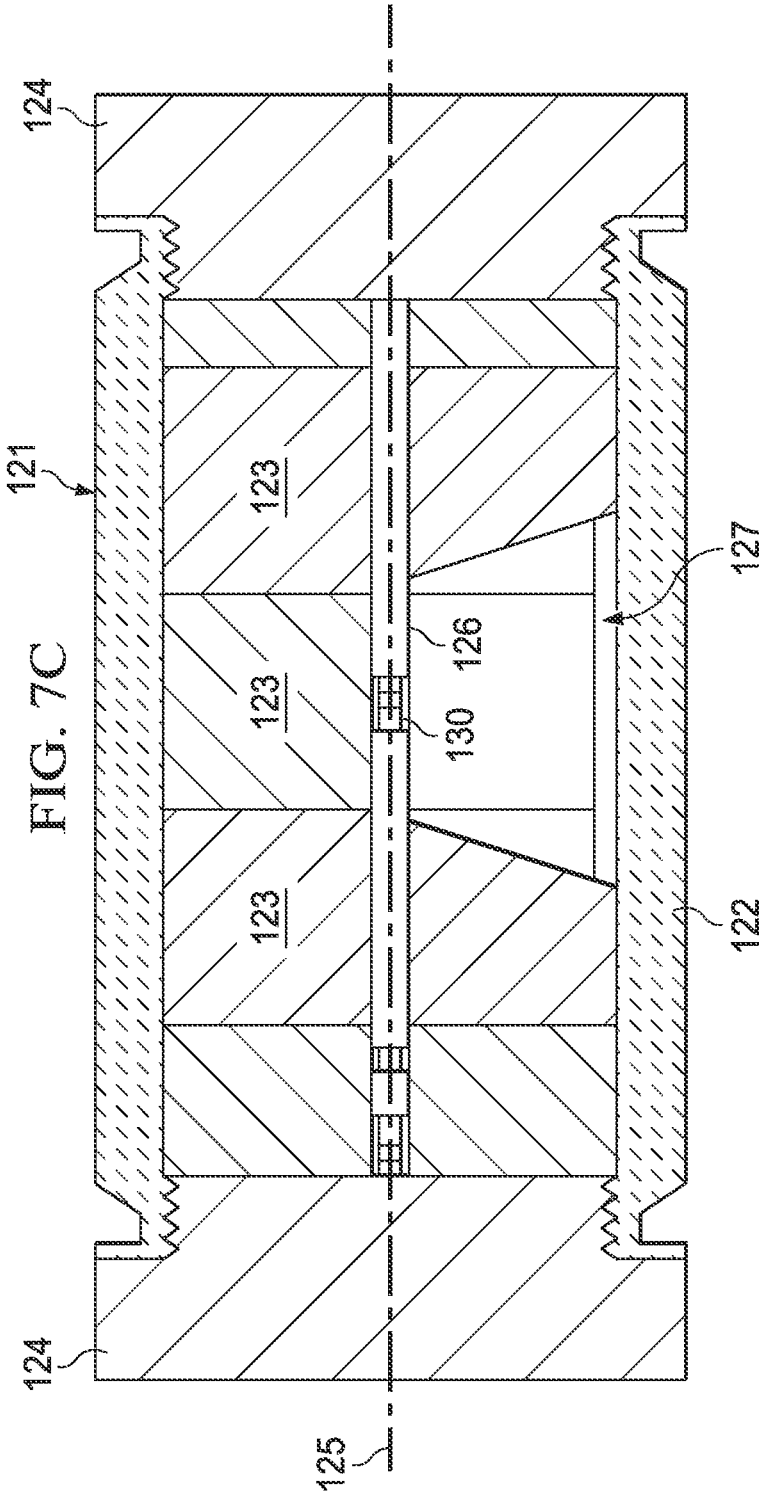

SYSTEM AND METHOD FOR UNDERWATER RADIOGRAPHY

CROSS-REFERENCE TO RELATED APPLICATIONS

This application claims benefit of U.S. provisional patent application Ser. No. 61/480,817 filed Apr. 29, 2011, and entitled "System and Method for Underwater Radiography," which is hereby incorporated herein by reference in its entirety for all purposes.

STATEMENT REGARDING FEDERALLY SPONSORED RESEARCH OR DEVELOPMENT

The United States government has rights in this invention pursuant to Contract No. DE-AC52-06NA25396 between the United States Department of Energy and Los Alamos National Security, LLC for the operation of Los Alamos National Laboratory.

BACKGROUND

1. Field of Technology

The disclosure relates generally to systems and methods of radiography. More particularly, the disclosure relates to systems and methods of perming underwater radiography, including at significant depths subsea.

2. Background Information

The basic principles of radiography are well-understood. Positioning an object of interest between a radiation source and a detector causes a portion of the electromagnetic radiation emitted from the source to be absorbed by the object and a portion to pass through the object, due to variations in density and composition of the object of interest. Electromagnetic radiation that is not absorbed by the object of interest may be captured by the detector, forming an image on the detector. The resulting image may then be processed and enhanced by various means. Different types of sources may be used in radiography, including X-ray producing X-ray tubes and gamma ray producing radioactive sources. Radioactive sources may be naturally occurring such as radium, mesothorium and the like, or artificial such as cobalt-60, iridium-192 and the like. Detectors may comprise film sensitive to electromagnetic radiation, phosphor coated imaging plates, or digital image capture devices such as flat panel detectors and high intensity line scan solid state detectors.

A very common application of radiography is in the medical field where it is used to allow physicians to visually observe the condition of bones and other features internal to a patient's body. Various types of electromagnetic radiation may be used in radiography, including x-rays and gamma rays, depending on the application. Because of its ability to create representations of the internal components of an object, industrial radiography has been employed in the analysis and non-destructive testing (NDT) of engineered structures, machines and other man-made products. For instance, industrial radiography may be used in testing and inspecting plate metal, pipe wall and welds on pressure vessels and conduits. Further, various techniques may be used in industrial radiography, including single wall exposure (SWE) techniques where the radiation source is placed internal of the object of interest, and double wall exposure (DWE) techniques where the source is placed externally on one side of the object of interest, with the imaging plate placed on the opposing side.

Underwater pipelines, cables, and products and structures associated with underwater oil and gas wells may require analysis and testing, specifically NDT. These objects may be located at the sea floor, which may be 5,000-7,000 feet or more below the surface, wherein the hydrostatic pressure of the water may exceed 2,000 pounds per square inch (PSI). Operating in such an environment may present unique challenges in which to attempt radiography, and may render certain conventional radiography equipment ineffective. For instance, ionizing radiation may be absorbed by the water, lengthening the necessary exposure time to form the radiographic image. Further, carrying out radiography at such depths requires that the underwater radiology system components be provided proximal to the sea floor and positioned by deep diving, remotely operated vehicles (ROVs) controlled by an operator at the surface. Not only may conventional radiography systems and components be unable to withstand the extreme pressures encountered in a subsea environment, but they may be too fragile to be handled by the manipulating arms of an ROV. Further, accurately controlling an ROV from substantial distances, and using an ROV to position and operate components of conventional radiography systems, may be impractical in many instances.

Accordingly, there remains a need in the art for apparatus, systems, and methods for conducting subsea radiography operations to image subsea equipment. Such apparatus, systems, and methods would be particularly well-received if they were suitable for use by ROVs in relatively deep see environments.

BRIEF SUMMARY OF THE DISCLOSURE

These and other needs in the art are addressed in one embodiment by a system for subsea imaging. In an embodiment, the system comprises a first plate having an inner surface, an outer surface, and a cavity formed in the inner surface. In addition, the system comprises a phosphor imaging plate disposed in the cavity. Further, the system comprises a second plate having an inner surface facing the inner surface of the first plate and an outer surface facing away from the outer surface of the first plate. Still further, the system comprises a seal member disposed between the inner surface of the first plate and the inner surface of the second plate. The seal member extends around the perimeter of the cavity and is configured to seal the phosphor imaging plate and the cavity from intrusion water.

These and other needs in the art are addressed in another embodiment by an apparatus for positioning a radiation source underwater for use in nondestructive testing. In an embodiment, the apparatus comprises a holder. In addition, the apparatus comprises a radiation source coupled to the holder. The radiation source is configured to emit radiation toward an object of interest. Further, the apparatus comprises at least one magnet coupled to the holder. The magnet is configured to hold the holder in position relative to the object of interest.

These and other needs in the art are addressed in another embodiment by a method for conducting radiography on a subsea object of interest. In an embodiment, the method comprises assembling an imaging cassette including an imaging plate sealed between a pair of support plates. In addition, the method comprises coupling a radiation source to a radiation source holder. Further, the method comprises positioning the radiation source holder in a first subsea location relative to the object of interest. Still further, the method comprises positioning the cassette subsea on the opposite side of the object of interest from the radiation source. Moreover, the method comprises irradiating the object of interest through the water disposed between the object of interest and the radiation source.

These and other needs in the art are addressed in another embodiment by an apparatus for use in underwater radiography. In an embodiment, the apparatus comprises a housing and a radiation source disposed in the housing. The housing includes an aperture. In addition, the apparatus comprises a shutter rotatably coupled to the housing. The shutter has a first position covering the aperture and a second position spaced away from the aperture.

These and other needs in the art are addressed in another embodiment by a method for performing underwater radiography. In an embodiment, the method comprises positioning a radiation source on a first side of an underwater object of interest. In addition, the method comprises positioning a radiation responsive apparatus capable of forming images in response to the receipt of radioactive emissions from the source on a second side of the underwater object of interest. The second side is opposite the first side. Further, the method comprises positioning a water purge device between the radiation source and the underwater object of interest. The water purge device a body having an internal chamber. Still further, the method comprises purging water from the chamber using a gas while the body is underwater.

Embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the disclosed embodiments of the invention, reference will now be made to the accompanying drawings in which:

FIG. 7C is a cross-sectional view of the source enclosure of FIGS. 7A and 7B;

DETAILED DESCRIPTION OF DISCLOSED EMBODIMENTS

The following description is exemplary of embodiments of the invention. These embodiments are not to be interpreted or otherwise used as limiting the scope of the disclosure, including the claims. One skilled in the art will understand that the following description has broad application, and the discussion of any embodiment is meant only to be exemplary of that embodiment, and is not intended to suggest in any way that the scope of the disclosure, including the claims, is limited to that embodiment.

The figures are not necessarily to scale. Certain features and components disclosed herein may be shown exaggerated in scale or in somewhat schematic form, and some details of conventional elements may not be shown in the interest of clarity and conciseness.

The terms "including" and "comprising" are used herein, including in the claims, in an open-ended fashion, and thus should be interpreted to mean "including, but not limited to . . . ." Also, the term "couple" or "couples" is intended to mean either an indirect or direct connection. Thus, if a first component couples or is coupled to a second component, the connection between the components may be through a direct engagement of the two components, or through an indirect connection that is accomplished via other intermediate components, devices and/or connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Figure 1:
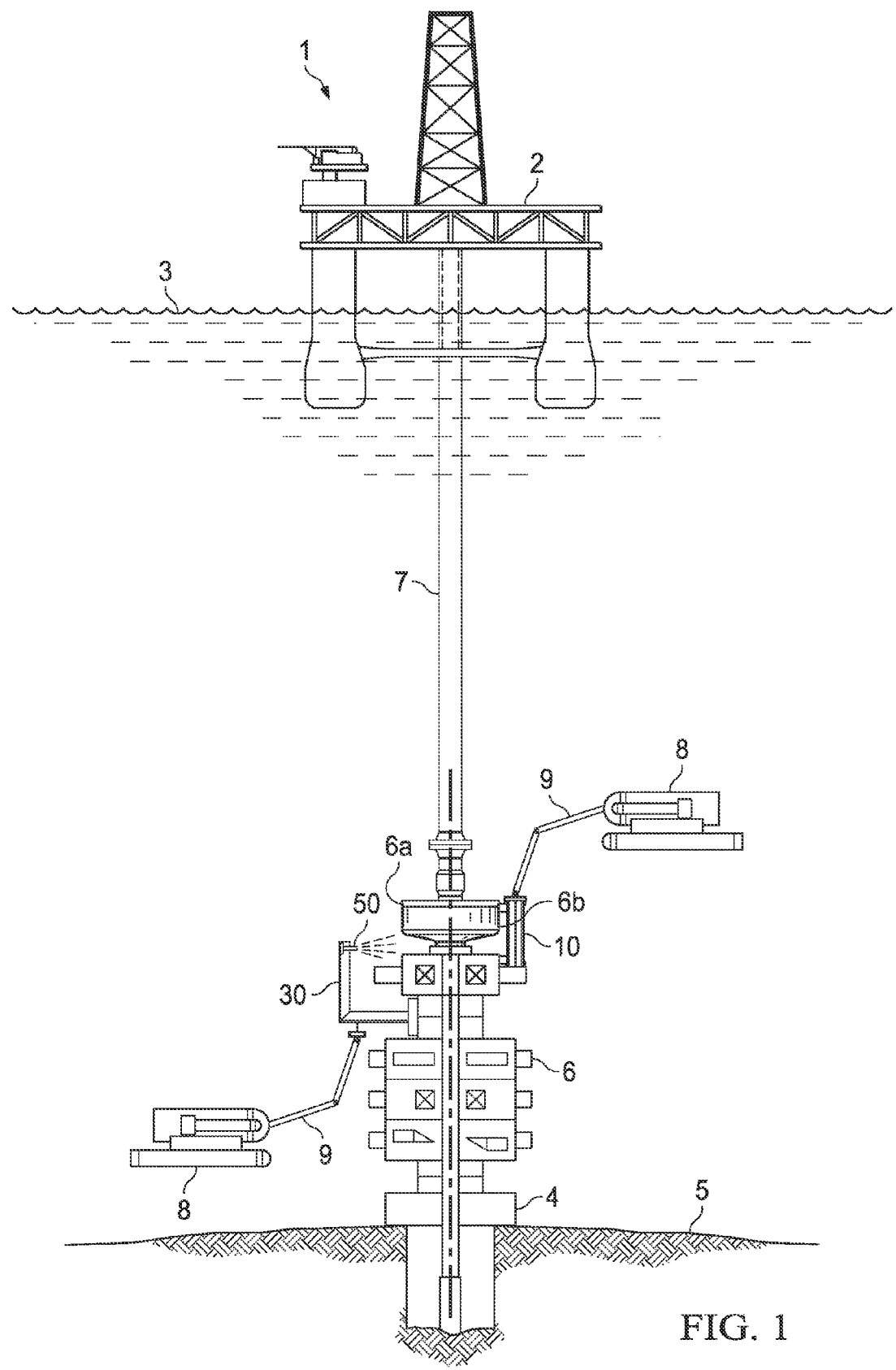
FIG. 1 is a schematic view of an embodiment of an underwater radiography system in accordance with the principles described herein.

Referring now to FIG. 1, an embodiment of an underwater radiography system 1 is shown. In this embodiment, system 1 comprises a surface vessel 2 disposed at the surface 3, a wellhead 4 disposed at the sea floor 5, a blowout preventer (BOP) 6 coupled to the wellhead 4, a riser 7 extending between the vessel 2 and BOP 6, a radiation source holder 30 and an imaging cassette 10 and a plurality of ROVs 8. BOP 6 has a first lateral side 6a and a second lateral side 6b opposite side 6a. In this embodiment, BOP 6 is the object of interest for which imaging is desired, and thus, BOP 6 is positioned between a radiation source 50 mounted to holder 30 and cassette 10—source 50 is positioned adjacent side 6a of BOP 6 and cassette 10 is positioned adjacent side 6b of BOP 6. As shown in FIG. 1, holder 30 and cassette 10 are each positioned by an ROV 8 using the ROV's manipulator arm 9.

In general, source 50 is configured to emit ionizing radiation in the direction of the object of interest and cassette 10. A portion of the emitted radiation from source 50 passes through the object of interest and a portion of the radiation absorbed by the object of interest. Cassette 10 is configured to receive the radiation that has passed through the object of interest. In this embodiment, BOP 6 is the object of interest, and thus, source 50 is configured to emit radiation in the direction of BOP 6 and cassette 10. Although BOP 6 is the object of interest in FIG. 1, in general, any piece of subsea equipment may serve as the object of interest such as riser 7 or wellhead 4. Further, although vessel 2 is depicted as a production rig in FIG. 1, in general, the surface vessel employed in embodiments described herein (e.g., vessel 2) may comprise any type of surface vessel, ship, boat, barge, platform, or the like.

Figure 2:
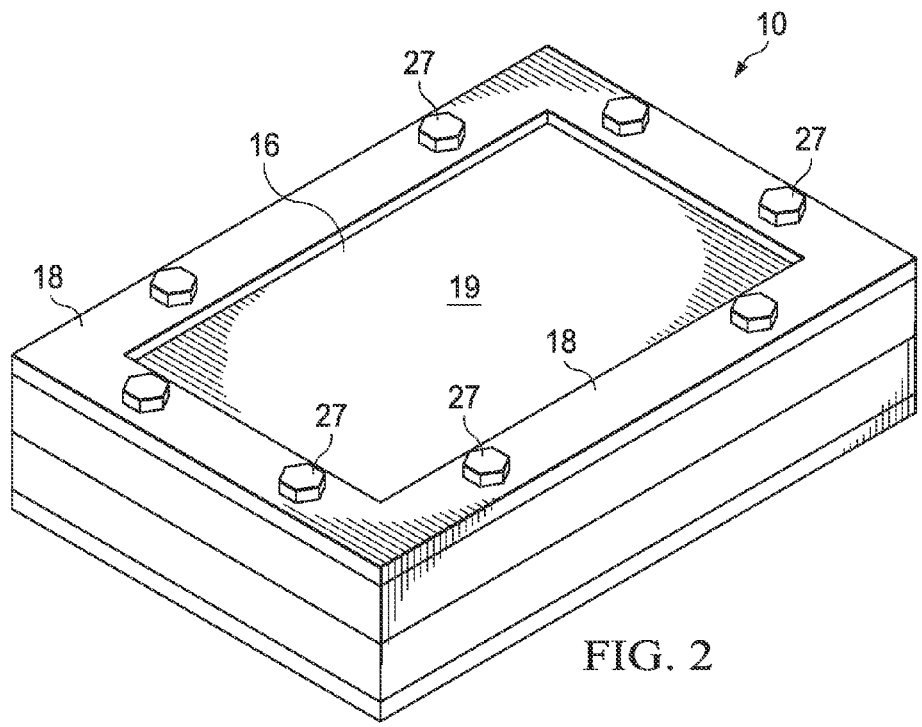
FIG. 2 is perspective view of the imaging cassette of FIG. 1.
Figure 3:
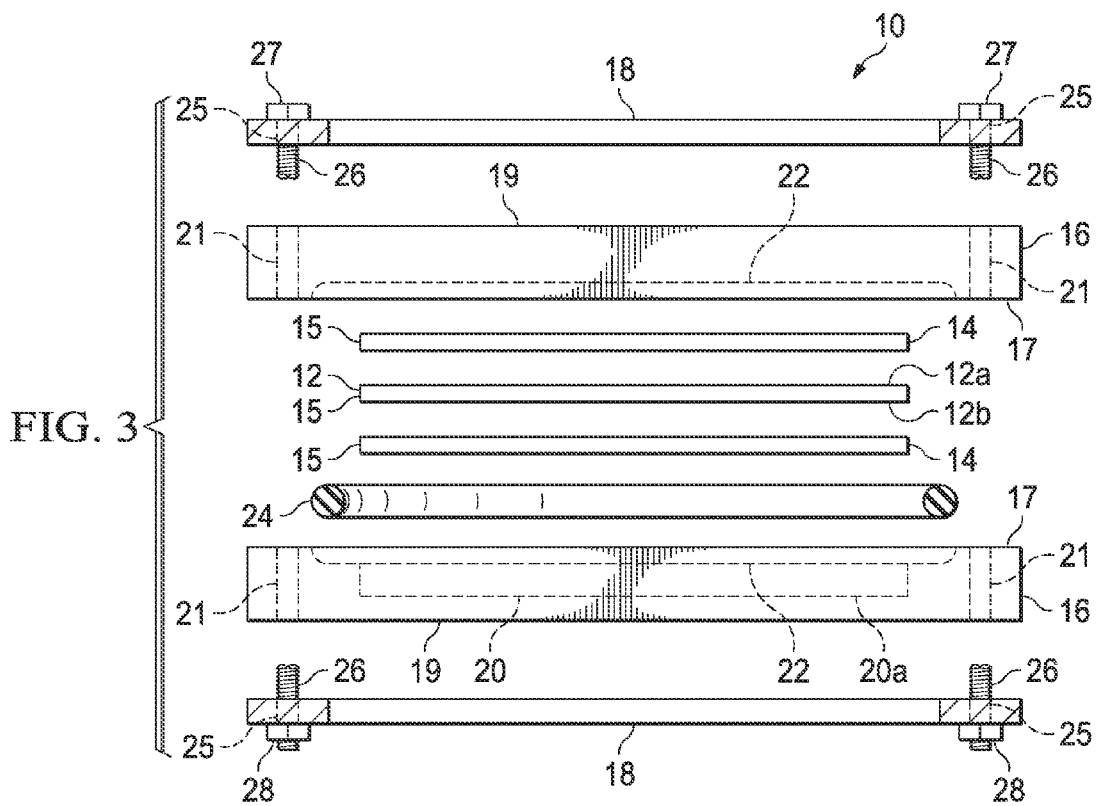
FIG. 3 is an exploded side view, partially in cross section, of the imaging cassette of FIG. 1.

Referring now to FIGS. 2 and 3, imaging cassette 10 comprises a phosphor imaging plate 12 having a first or upper side 12a and a second or lower side 12b opposite side 12a, a pair of intensifying screens 14, a pair of protective and supporting plates 16, and a pair of frame members 18. Imaging cassette 10 is configured for utilizing phosphor imaging plate 12 subsea, particularly at great depths below the surface, protecting plate 12 during handling and transport between the surface and the subsea site of the object of interest, and sealing the plate 12 from water when submerged.

In this embodiment, phosphor imaging plate 12 is a generally rectangular plate coated with phosphor particles that, when exposed to radiation, forms a metastable state that can be read out at a later time to form a viewable image. For instance, data contained by plate 12 may be used to form a radiographic image of the portion of BOP 6 irradiated by source 50 of FIG. 1, possibly through digitizing the stored analog signal in a computed radiography scanner. Plate 12 may be any standard phosphor imaging plate, with plates having smaller phosphor grain sizes providing better definition. An example of a plate 12 suitable for use in embodiments described herein is supplied by General Electric Company and designated as an IPU high performance Storage Phosphor Imaging plate, having model designator IPC-2.

To enhance the image created on phosphor imaging plate 12, plate 12 is sandwiched between the pair of intensifying screens 14. For instance, the intensity of electromagnetic radiation emitted from source 50 of FIG. 1 may be attenuated as it passes through an object of interest, such as BOP 6, due to absorption of the radiation by the object and scattering of the radiation as it passes through the object. Further, materials in the vicinity of the radiation source 50 may form a "back scatter" effect on the imaging plate due to the radiation being reflected and scattered as it passes through the neighboring material, reducing the quality of the radiographic image formed on plate 12. However, intensifying screens 14 have the effect of increasing the photographic response of the phosphor imaging plate 12 such that the image can be created on the imaging plate 12 in a significantly shorter exposure time than would otherwise be required. For instance, intensifying screens 14 may be configured to increase the portion of radiation emitted by radiation source 50 of FIG. 1 utilized by imaging plate 12 during the process of forming a radiographic image. In addition, an intensifying screen is useful in reducing the detrimental effect of radiation scatter. Specifically, intensifying screens 14 are configured for intercepting scattered radiation. Further, intensifying screens 14 may reduce blurring caused by Compton scattered electrons. In the embodiment shown, intensifying screens 14 are made of tantalum, however, other materials may be employed, including platinum, lead and the like.

In this embodiment, intensifying screens 14 have the same size and geometry as the phosphor imaging plate 12. In particular, screens 14 and plate 12 are rectangular, each having the same width and length. As previously described, plate 12 is positioned between screens 14. More specifically, one intensifying screen 14 engages first side 12a of imaging plate 12 and the other intensifying screen 14 engages second side 12b of imaging plate 12. The configuration of screens 14 and plate 12 forms a stacked plate assembly 15.

Although screens 14 and plate 12 having the same size and geometry in this embodiment, in other embodiments, the size and/or shape of the intensifying screens (e.g., screens 14) and the imaging plate (e.g., plate 12) may vary. Further, although two intensifying screens 14 are employed in the exemplary embodiment illustrated in FIGS. 2 and 3 for the reasons stated above, in other embodiments, a single intensifying screen (e.g., screen 14) may be used. In such an embodiment, the single intensifying screen engages the side of the imaging plate (e.g., plate 12) that faces the radiation source (e.g., source 50).

To protect phosphor imaging plate 12 and intensifying screens 14 from physical damage, such as damage resulting from hydrostatic subsea pressures, as well as to seal those elements from water, assembly 15 is sealed between a pair of protective support plates 16. Each plate 16 includes an inner surface 17 facing imaging plate 12 and an outer surface 19 facing away from imaging plate 12. Support plates 16 are made of material(s) suitable for use subsea, and preferably have a relatively high strength-to-weight ratio and suitable radiation transmission characteristics. In this embodiment, plates 16 are formed of aluminum. Aluminum provides sufficient strength but, at the same time, is relatively lightweight and thus more easily handled than stronger but heavier materials (e.g., steel). Aluminum is also a low-Z material and therefore has provides good radiation transmission characteristics. Other materials having similar or even better strength-to-weight ratios than aluminum, such as titanium, carbon fiber, and polycarbonate may also be used to form support plates 16.

As best shown in FIG. 3, one support plate 16 includes a recess or cavity 20 extending perpendicularly from facing surface 17 and configured to receive assembly 15. In other embodiments, both support plates (e.g., plates 16) may include a recess in its inner surface (e.g., surface 17) that together define a cavity for housing the imaging plate (e.g., plate 12) and intensifying screens (e.g., screens 14). In either case, the total depth of cavity 20 is slightly less than the combined thickness of phosphor imaging plate 12 and both intensifying screens 14. In addition, each support plate 16 includes a seal groove 22 formed in facing surface 17 of the corresponding plate 16. Groove 22 extends entirely around the perimeter of the assembly 15. An elastomeric seal 24 having a circular cross-section is seated in groove 22. Seal 24 extends entirely around the perimeter of assembly 15. Suitable materials for seal 24 include Viton® fluoroelastomer. In other embodiments, the seal groove (e.g., seal groove 22) is disposed on only one support plate (e.g., plate 16) such that the seal (e.g., seal 24) engages the planar inner surface (e.g., surface 17) of the opposite plate that does not include a groove. Plates 16 also a plurality of bores 21 disposed about the outer perimeter of plates 16 for receiving bolts 27 that hold cassette 10 together.

Referring still to FIGS. 2 and 3, one frame member 18 is disposed about the perimeter of the outer surface 19 of each plate 16. Each frame member 18 has a picture frame-configuration that, in this embodiment, is formed of ferro-magnetic metal, although other materials may be employed. Frame members 18 provide additional rigidity to cassette 10 as well as provides a means for handling and attaching cassette 10 to underwater structures, as will be described in more detail below. Each frame member 18 comprises a plurality of spaced holes 25. Bolts 27 are disposed in holes 25. Each bolt 27 includes a shank 26 and a corresponding nut 28. Shanks 26 of bolts 27 extend through the sets of aligned holes 25 in frame members 18 and the bores 21 of each plate 16.

The assembly of cassette 10 will now be described with reference to FIG. 3. To assemble cassette 10, a first intensifying screen 14 is positioned within cavity 20, with a side of that screen 14 engaging the corresponding support plate. Next, phosphor imaging plate 12 is placed in cavity 20 on top of the first intensifying screen 14, and the second intensifying screen 14 is placed in cavity on top of the imaging plate 12. Thus, phosphor imaging plate 12 is disposed between the two intensifying screens 14, thereby forming assembly 15 within cavity 20. As previously described, the combined thickness of the two screens 14 and plate 12 slightly exceed the depth of cavity 20. Next, seal 24 is placed in seal groove 22 of the support plate 16 housing assembly 15, and the second support plate 16 is then disposed atop assembly 15 and the support plate 16 housing assembly 15. A frame member 18 is then placed about the perimeter of each plate 16, and the threaded shanks 26 of bolts 27 are disposed through aligned holes 25 formed in frame members 18 and bores 21 formed in support plates 16. Nuts 28 are threaded onto shanks 26 and torqued down to compress support plates 16 together, compress seal 24, and compress assembly 15. In the embodiment shown in FIG. 3, prior to tightening nuts 28, the two plates 16 are preferably squeezed together so as to compress the assembly 15 completely into cavity 20. In this manner, substantially all air previously disposed within cavity 20 is evacuated from cavity 20. In general, to provide conditions allowing for the best radiographic image quality, water is preferably prevented water from entering cavity 20, and further, the amount of any air within cavity 20 after assembly of cassette 10 is also preferably minimized. Accordingly, cavity 20 is sized so as to be only slightly larger in length and width than the phosphor imaging plate 12 and intensifying screens 14 such that there remains little volume in cavity 20 that is not occupied by assembly 15 upon the disposal of assembly 15 in cavity 20.

In the embodiment of cassette 10 previously described, one imaging plate 12 is provided in cavity 20. However, in other embodiments, more than one imaging plate (e.g., plate 12) may be provided in the cassette (e.g., cassette 10). In such embodiments, the cavity (e.g., cavity 20), which may be formed in one or both of the support plates (e.g., plates 16), houses a stack of multiple imaging plates and intensifying screens (e.g., screens 14) in an alternating pattern (e.g., an intensifying followed by an imaging plate 12, followed by another intensifying screen, followed by another imaging plate, and so on). An intensifying screen is preferably disposed at each end of the stack such that the support plates are in physical engagement with a pair of intensifying screens upon assembly. Using such a stack would allow for the accumulation of electromagnetic signal from more than a single intensifying screen, thereby offering the potential to increase the final image quality and/or lowering the necessary exposure time. This may be particularly useful in applications where the object of interest is relatively thick and/or when relatively low exposures are used.

Figure 4:
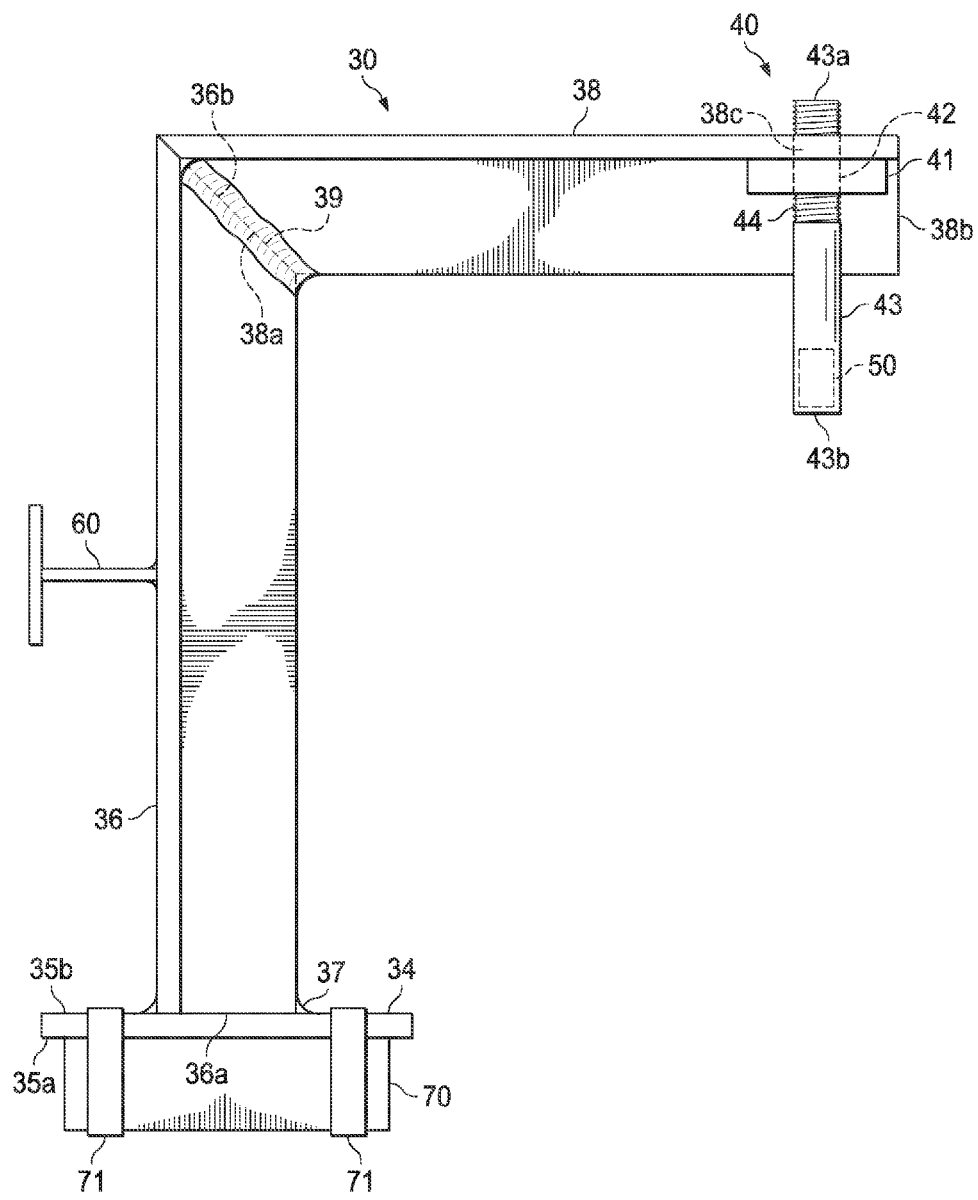
FIG. 4 is a side view of the underwater radioactive source holder of FIG. 1.

Referring now to FIG. 4, radiation source holder 30 is shown. In this embodiment, source holder 30 includes a base flange 34, a pillar 36 coupled to flange 34, an arm 38 coupled to pillar 36, and a magnet 70 coupled to the base flange 34 with a plurality of straps 71. Flange 34 has a first or lower planar surface 35a and a second or upper planar surface 35b oriented parallel to surface 35a. Pillar 36 extends perpendicularly from upper surface 35b and magnet 70 engages lower surface 35a. Pillar 36 is a rigid, straight member having a first or lower end 36a welded to base flange 34 at joint 37 and a second or upper end 36b opposite end 36a. In this embodiment, pillar 36 has an L-shaped cross-section. In addition, in this embodiment, a handle 60 is attached to pillar 36. Handle 60 is configured to be grasped by a subsea ROV (e.g., ROV 8) to enable the ROV to manipulate, orient, and position holder 30 as desired. Although handle 60 is shown as a T-handle secured to pillar 60, in other embodiments, the handle (e.g., handle) may take other forms and/or be attached to other parts of the radiation source holder (e.g., holder 30).

Support arm 38 is a is a rigid, straight member extending perpendicularly from pillar 36 and having a first end 38a welded to end 36b of pillar 36 at a joint 39 and second end 38b distal pillar 36. In this embodiment, support arm 38 has an L-shaped cross-section. Although pillar 36 and support arm 38 each have an L-shaped cross-section in this embodiment, in general, the pillar (e.g., pillar 36) and the support arm (e.g., support arm 38) may have other geometries such as rectangular, circular, or triangular cross-sections.

Radiation source 50 is coupled to end 38b of arm 38 with a source attachment mechanism 40. In this embodiment, source attachment mechanism 40 includes a block 41 having a threaded through bore 42 and a cylindrical enclosure or housing 43 threaded into bore 42 of block 41. Bore 42 is coaxially aligned with a bore 38c in end 38b of arm 38. Housing 43 is an elongate member having an externally threaded first end 43a and a second end 43b opposite end 43a. Threaded end 43a threadably engages mating internal threads in bore 42 and extends through bore 38c, thereby releasably coupling housing 43 to block 41 and arm 38. Radiation source 50 is disposed within a cavity formed within end 43b of housing 43. In general, radiation source 50 may comprise any suitable source of radiation. However, in this embodiment, source 50 is a Cobalt-60 source that provides an un-collimated 290 milliCurie (mCi) radioactive emission. Such a source is available from Tracerco Limited of Pasadena, Tex., the source being identified by Tracerco Limited as a Gamma Densitometer pencil source housed in a sealed container rated as water tight up to 10,000 ft.

Referring still to FIG. 4, as previously described, magnet 70 is secured to base flange 53 in this embodiment. In particular, the pair of straps 71 compress magnet 70 against planar surface 35a of base flange 34. As will be described in more detail below, magnet 70 facilitates the positioning of holder 30 during subsea imaging operations. Although magnet 70 may comprise any suitable type of magnet(s), in this embodiment, magnet 70 is a rare earth Neodymium-Iron magnet having a pull force rating of 400 pounds (lbs). Such magnets are available from a variety of sources, including, for example, Dura Magnetics, Inc. of Sylvania, Ohio.

Referring now to FIGS. 1 and 4, pillar 36 has a length measured between ends 36a, b that is selected to provide an appropriate distance between radiation source 50 and cassette 10. For example, in this embodiment, pillar 36 has a length of 18 in. It should be appreciated that the position of radiation source 50, and hence length of pillar 36, may be dictated, at least in part, by the clearances available to perform the subsea radiography. That is, other underwater structures adjacent the object of interest, or portions of the object of interest at the location where it is desired to perform the radiography, may restrict or limit the positioning of the radiation source 50 and cassette 10. Accordingly, source holder 30 provides a standoff distance between radiation source 50 and BOP 6, with the standoff distance being variable, depending on the specific radiography application.

Referring again to FIG. 1, an embodiment of a method of deploying cassette 10 and source holder 30 to perform subsea radiography operations will be described. In this embodiment, the object of interest is BOP 6, however, as noted above, the object of interest may be any subsea device or structure for which radiographic imaging is desired (e.g., BOP, manifold, pipeline, etc.). Imaging cassette 10 and radiation source holder 30 are lowered subsea from a surface vessel 2 to the object of interest. For instance, imaging cassette 10 and source holder 30 may be transported subsea from vessel 2 via a wireline and/or subsea ROV 8. Although air that existed in cavity 20 was, to a large degree, expelled during assembly of cassette 10, particularly as the fasteners were tightened and intensifying screens 14 and imaging plate 12 were compressed into cavity 20 by plates 16 (FIG. 3), deploying imaging cassette 10 to depths where pressures gradually build to hundreds and thousands of PSI compresses plates 16 together further, slightly decreasing the volume of cavity 20 and compressing the air therein. In some cases, some of the air within cavity 20 may be expelled from cavity 20. To reduce and/or eliminate the potential to compromise or damage seal 24 in cases where air is allowed to escape cavity 20, a deep water pressure relief valve is preferably included with cassette 10 and placed in fluid communication with cavity 20 to control the release of the air from cavity 20. One example of a suitable deep water pressure relief valve is the titanium PREVCO Pressure Relief Valve available from PREVCO Subsea Housings of Fountain Hills, Ariz.

Figure 5:
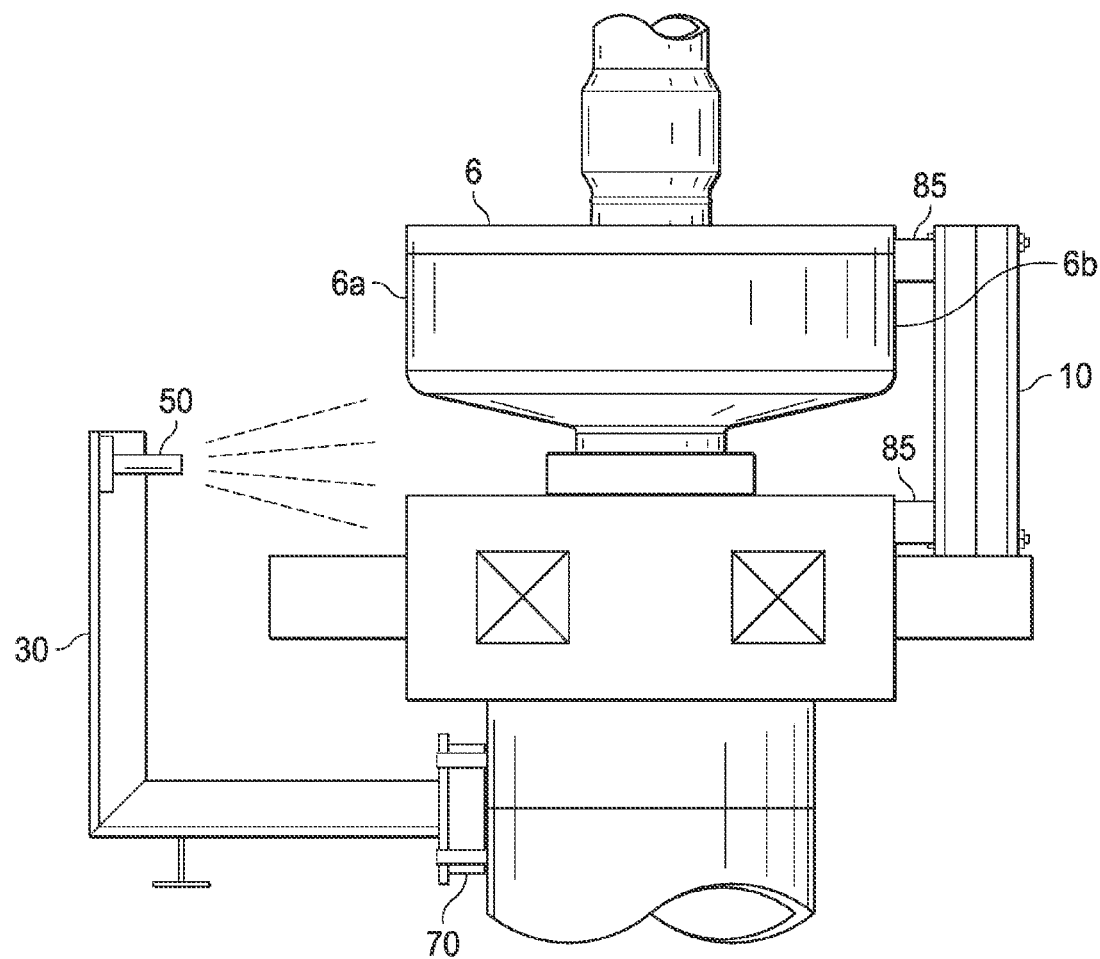
FIG. 5 is a schematic view of the radiography system of FIG. 1 including an alternative means of deployment.

Once "on site," imaging cassette 10 and holder 30 are disposed on opposite sides of the object of interest. Thus, in this embodiment, cassette 10 and holder 30 are positioned on opposite sides of BOP 6. In particular, holder 30 (and source 50) are positioned adjacent side 6a and cassette 10 is positioned adjacent side 6b. Imaging plate 12 is preferably maintained as still as possible during subsea imaging, and thus, cassette 10 is preferably held in position with as little movement as possible while imaging plate 12 is being exposed. Securing imaging cassette 10 in position may be accomplished in several ways. For instance, as shown schematically in FIG. 1, imaging cassette 10 is held in place by manipulator arm 9 of ROV 8. Frame member 18 provides ROV 8 with a convenient and relatively stiff handle for manipulating and holding imaging plate 10 in position. In practice, ROV 8 will often first secure itself to the object of interest (e.g., BOP 6) or another fixed structure by a second manipulator arm (not shown), and then will position the imaging cassette 10 using arm 9. This approach offers the potential to minimize movement of ROV 8 and cassette 10 during imaging operations. Referring briefly to FIG. 5, as an alternative to holding cassette 10 in place via ROV 8, magnets 85 similar to magnets 70 previously described (e.g., rare earth magnets of Neodymium-Iron having substantial magnetic strength) may be attached to cassette 10 and used to mount cassette 10 to the object of interest. Frame member 18 made of a ferro-magnetic metal for example, provides a means to magnetically couple cassette 10 to BOP 6 or to another nearby support structure.

Referring again to FIG. 1, although radiation source 50 is sealed within water tight enclosure 43, it is unshielded, and thus, is continuously emitting electromagnetic radiation to the surrounding environment. As such, imaging plate 12 will be subject to exposure from source 50 as soon as it is in the vicinity of source 50. Thus, after imaging plate 12 has been positioned, radiation source holder 30 is preferably moved into position as quickly as possible to facilitate the production of an accurate image. Optionally, source holder 30 may first be positioned, followed by the step of securing imaging cassette 10 in position, again as quickly as reasonably possible. As a further option, a shield can be temporarily placed between source 50 and imaging plate 12 to minimize exposure of plate 12 during deployment and positioning of cassette 10 and holder 30. Suitable shield materials include, but are not limited to iron, lead, and tungsten. Such a shield can be relatively small if placed proximal source 50.

With imaging cassette 10 in position, an ROV 8 uses handle 60 to position radiation source holder 30 in the desired position as quickly as reasonably possible. In some methods, ROV 8 itself will position and hold the radiation source holder 30 in an appropriate location during the duration of the radiography process, however, in such embodiments, that ROV 8 is unavailable for other tasks. Accordingly, as shown in FIG. 5, magnet 70 is used to position and retain radiation source holder 30 in a desired position proximal first side 6a of BOP 6 opposite imaging cassette 10. Magnet 70 provides a strong holding means useful to position on a ferro-magnetic metal structure, such as BOP 6. Once positioned and secured via magnet 70, ROV 8 can release radiation source holder 30 and be used for other operations. Imaging cassette 10 and radiation source holder 30 remain in this position for a predetermined period of time required to properly expose imaging plate 12 with radiation emitted from source 50, such that a suitable radiographic image may be produced. In this embodiment, using the Cobalt-60 radiation source 50 described above, and with the radiation source 50 positioned approximately 18 inches from side 6a of BOP 6, the exposure time is preferably greater than 10 minutes, and more preferably at least 20 minutes. For most applications, exposure times of 25-30 minutes or more are preferred, depending on a variety of factors including, without limitation, the type of source 50 used, the structure and composition of the object of interest, and the distances between the object of interest and the cassette 10 and source 50. As compared to radiography above the surface of the water, the exposure times underwater are significantly greater. At least in part, the greater exposure time needed is due to the significant attenuation of the radiation as it passes through the expanse and volume of water that separates the radiation source 50 and the object of interest (BOP 6 in FIG. 1). A stronger radiation source than source 50 may also be employed, such as a 1 Ci source, which would shorten the necessary exposure time. Commercially available sources vary in strength from micro-Curie range to Curie strength. As mentioned previously, the imaging plates 12 described herein are coated with phosphor particles. However, such storage phosphors do not suffer reciprocity failure until the exposure time exceeds an hour or more. By contrast, ordinary x-ray film suffers from reciprocity failure during such long exposures, thereby limiting its utility to short duration applications.

Referring again to FIGS. 1 and 5, after an appropriate length of time has passed to allow phosphor imaging plate 12 to be exposed to sufficient radiation from source 50, imaging cassette 10 and radiation source holder 30 are removed from the object of interest with ROVs 8 and returned to the surface vessel 2. In general, the amount of exposure time necessary may vary depending on a variety of factors including, without limitation, the strength of source 50, the physical geometry and layout of system 1, and radiation attenuation. At the surface, imaging plate 12 is processed through known "scanning" methods in order to form a viewable radiographic image. The data that has permitted the image to be formed is "stored" in the phosphor particles of imaging plate 12 during the process of irradiating imaging plate 12. Thus, the phosphor particles of plate 12 serve essentially as an analog memory medium. Unlike other detectors such as digital radiography (DR) plates, storage phosphors do not accumulate electronic noise. Another advantage of storage phosphors is that they do not require power to function and can be formed into any desired size and shape. To minimize continued exposure of plate 12 to source 50 during retrieval to the surface, cassette 10 and holder 30 are preferably sufficiently separated (i.e., spaced apart) during retrieval to the surface or retrieved separately.

Figure 6:
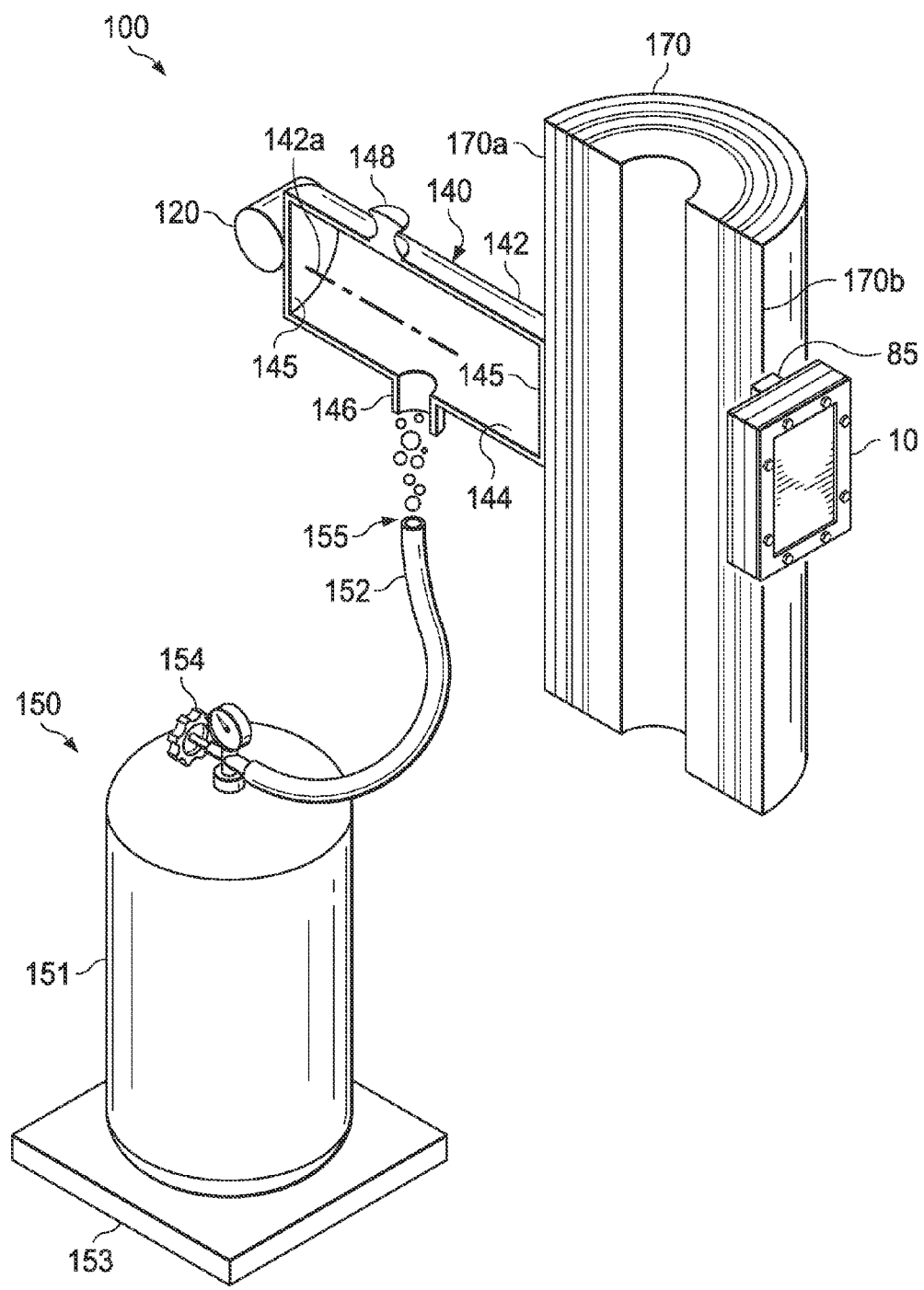
FIG. 6 is a schematic view, partly in cross section, of an embodiment of an underwater radiography system in accordance with the principles described herein.

Referring now to FIG. 6, another embodiment of a subsea radiography system 100 is shown. In this embodiment, system 100 includes a shuttered radiation source holder 120, a water purge or exclusion device 140, a gas supply 150, and an imaging cassette 10 as previously described.

Figure 7A:
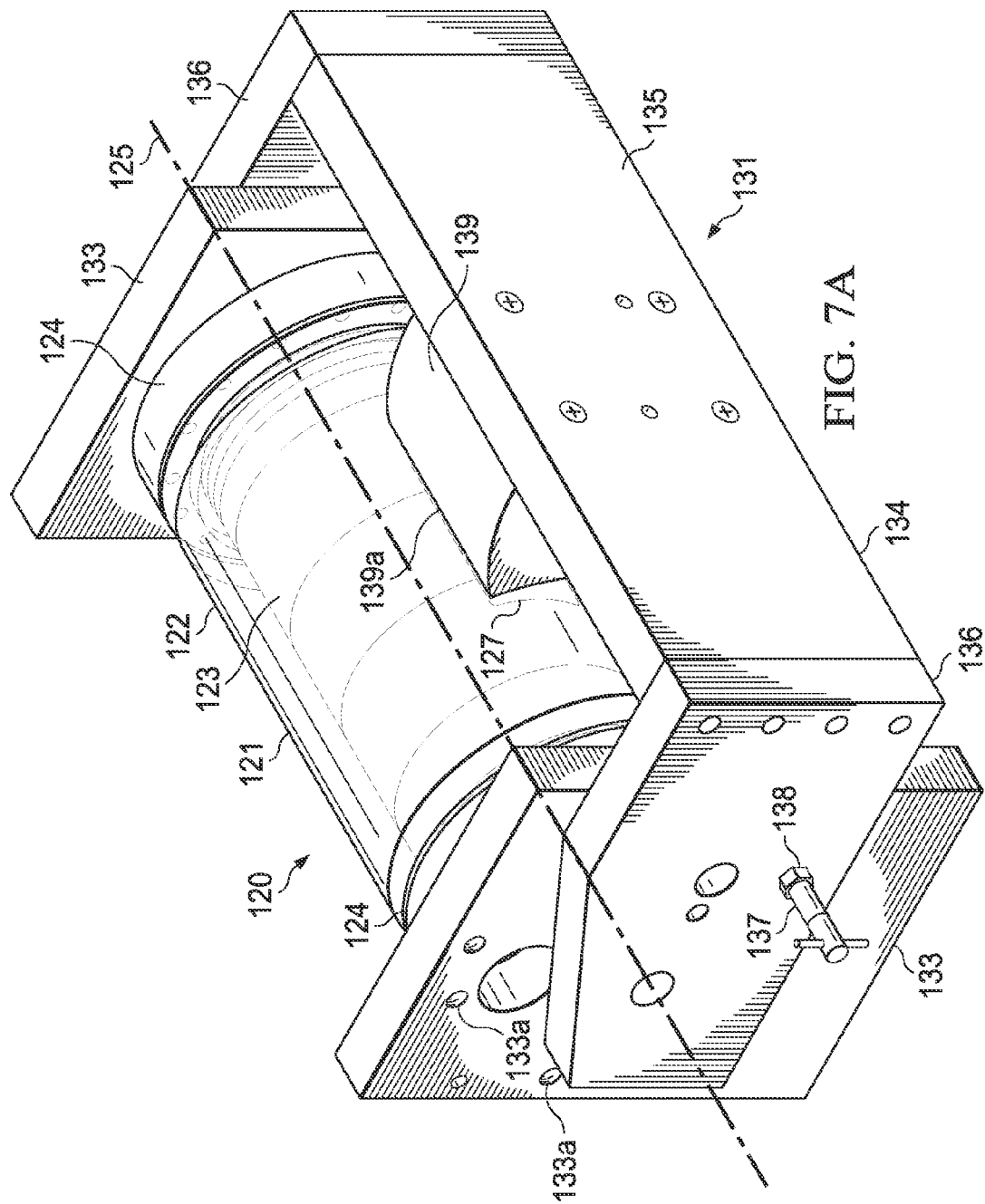
FIG. 7A is a perspective view of the shuttered radiation source holder of FIG. 6 with the shutter in a "closed" position.
Figure 7B:
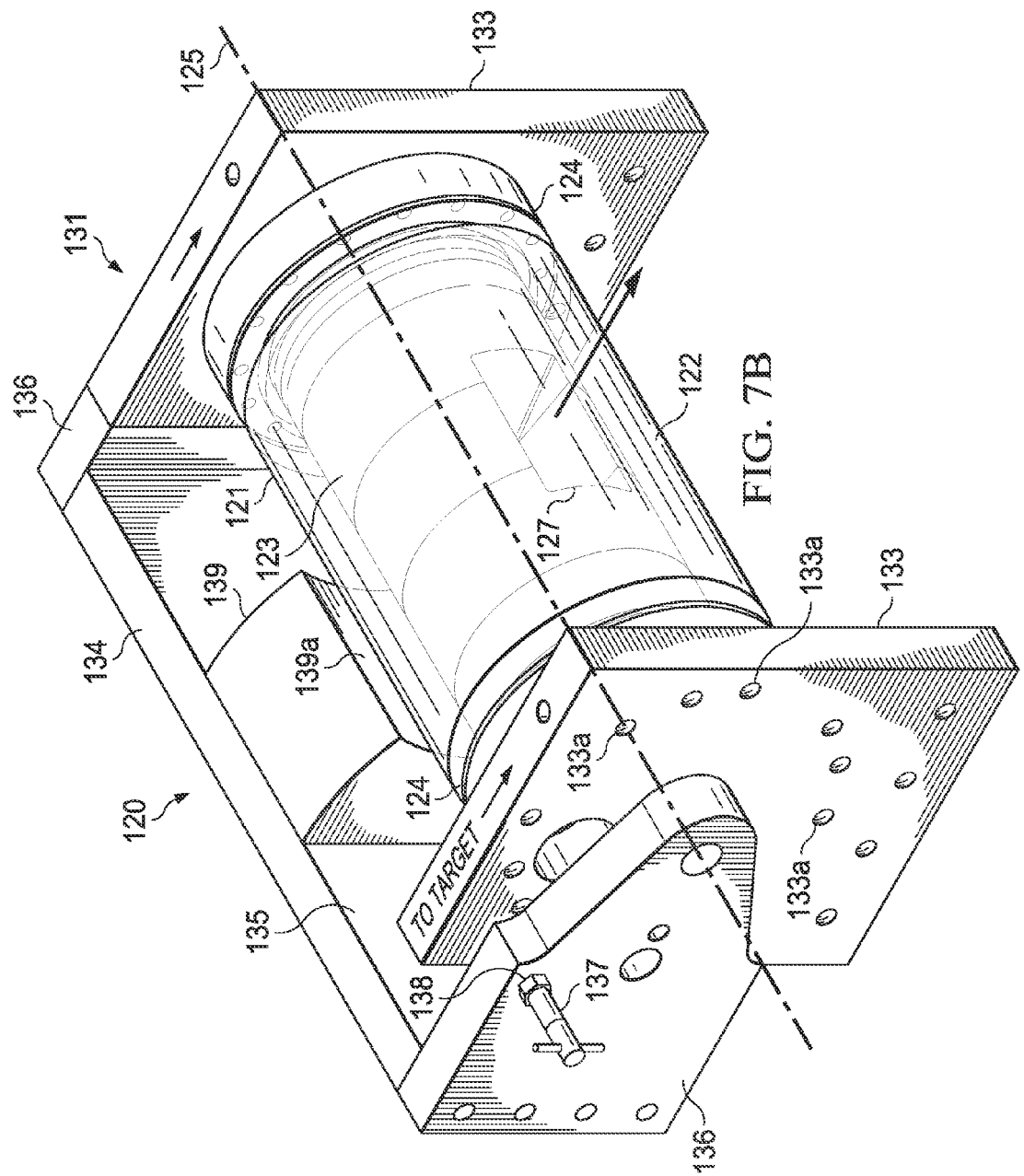
FIG. 7B is a perspective view of the shuttered radiation source holder of FIG. 6 with the shutter in an "open" position.

As best shown in FIGS. 7A, 7B, and 7C, shuttered holder 120 includes a source enclosure or housing 121, a radiation source 130 disposed within housing 121, and a shutter assembly 131 coupled to housing 121. Housing 121 provides a water right enclosure for source 130. As will be described in more detail below, shutter assembly 131 selectively blocks the emission of radiation from source 130. In this embodiment, housing 121 has a central or longitudinal axis 125 and includes a radially outer tubular shell 122, shielding 123 disposed within shell 122, and a pair of end caps 124 removably coupled to shell 122. In particular, one end cap 124 is threaded to each axial end of shell 122, thereby maintaining shielding 123 within shell 122. For purposes of clarity, shell 122 is shown as transparent in FIGS. 7A and 7B so that shielding 123 therein can be seen, however, shell 122 need not be made of a transparent material. Shielding 123 slidingly engages shell 122 and extends axially between end caps 124. Thus, shielding 123 has an outer radius that is substantially the same or slightly less than the inner radius of shell 122. In this embodiment, shielding 123 is modular. Namely, shielding is formed from a plurality of axially adjacent generally cylindrical segments coupled together end-to-end.

As best shown in FIG. 7C, shielding 123 includes a central through bore 126 extending axially therethrough (i.e., from one end of shielding 123 to the opposite end of shielding 123) and a radiation collimating aperture 127 extending radially from the mid-point of bore 126 to the radially outer surface of shielding 123 and shell 122. Source 130 is a generally cylindrical slug that is axially inserted into bore 126 and positioned at the mid-point of bore 126 (i.e., at the intersection of aperture 127 and bore 126). In this embodiment, source 130 is a high-energy, high activity radioactive gamma source such as Cobalt 60. Aperture 127 is a tapered extruded rectangular passage—the width and height of aperture 127 increases moving radially from bore 126 to shell 122. Thus, aperture 127 is shaped like a rectangular horn.

In general, shielding 123 blocks the radiation emitted from source 130. However, due to the absence of shielding material in aperture 127, radiation is free to pass through aperture 127 without restriction. In this manner, aperture 127 functions to collimate the radiation emitted from source 130. The radiation passing through aperture 127 can also pass through shell 122 as it does not substantially block or attenuate radiation. Thus, radiation from source 130 is allowed to pass radially outward through aperture 127 and through shell 122 in a general direction aligned with the central axis of aperture 127, but is blocked in all other directions by shielding 123. In general, shielding 123 may comprise any suitable radiation shielding material, but is preferably made of a high-Z material, such as iron, tungsten, alloys of iron or tungsten, or other high-Z materials. In this embodiment, shielding 123 is made of a tungsten alloy having approximately 95% tungsten, with the remaining constituents being nickel and iron to allow the material to be more easily machined into the desired shape.

Referring again to FIGS. 7A and 7B, shutter assembly 131 includes a pair of connection members or end plates 133 secured to housing 121 and a rotatably shutter 134 rotatably coupled to connection members 133 and housing 121. In particular, one connection member 133 is fixably attached to each end cap 124 of housing 121. Rotatable shutter 134 includes a central portion or base 135 and a pair of arms 136 attached to base 135. Base 135 is a plate oriented parallel to axis 125, radially spaced from axis 125, and has a length slightly greater than the axial length of housing 121. Arms 136 extend perpendicularly from the ends of base 135 and radially inward (relative to axis 125) to end plates 122. Accordingly, arms 136 are positioned axially adjacent the outer surfaces of end caps 124. Each arm 136 is pivotally pinned to the corresponding connection member 133 such that shutter 134 rotates about axis 125 relative to housing 121. At least one arm 136 includes a locking pin 137 disposed in a mating through bore 138 in arm 136. Pin 137 is configured to be moved axially relative to arm 136 into and out of engagement with any one of a plurality of circumferentially spaced mating bores 133a in the adjacent connection member 133. In this embodiment, pin 137 includes external threads that mate and threadingly engage internal threads in bores 138, 133a. Thus, pin 137 can be threaded through bore 138 and into any one of bores 133a that is aligned with bore 138 to selectively lock the circumferential position of shutter 134 relative to housing 121.

In this embodiment, rotatable shutter 134 also includes an aperture cover 139 mounted to base 135 at the midpoint between arms 136 and radially positioned between base 135 and housing 121. Thus, cover 139 is positioned to cover and close off aperture 127 when shutter 134 is rotated to place cover 139 into alignment with aperture 127. In this embodiment, cover 139 has a concave cylindrical radially inner surface 139a disposed at a radius (relative to axis 125) that is substantially the same or slightly greater than the outer radius of shell 122 and housing 121, thereby allowing cover 139 to slidingly engage shell 122 and housing 121 as shutter 134 is rotated relative to housing 121. Cover 139 is made of, or coated with, a relatively high Z radiation shielding material such as iron, tungsten, or alloys thereof. Thus, by rotating shutter 134, cover 139 is employed to cover and uncover aperture 127 as desired to allow or block radiation emitted therefrom. In particular, shutter assembly 131, shutter 134, and cover 139 have a first or closed position with cover 139 disposed over and in radial alignment with aperture 127 as shown in FIG. 7A, and a second or open position with cover 139 circumferentially spaced from and out of radial alignment with aperture 127 as shown in shown in FIG. 7B. In the open position, radiation from source 130 is emitted through aperture 127 and shell 122 in a geneal direction aligned with the central axis of aperture 127 for use in creating a radiographic image with imaging cassette 10, and in the closed position, cover 139 substantially blocks the radiation emitted through aperture 127 such that the radiation source may effectively be considered turned "off."

Referring again to FIG. 6, water purge device 140 is positioned adjacent source holder 120 between holder 120 and the object of interest. In general, purge device 140 can be attached or tethered to holder 120, the object of interest, an anchor on the sea floor, or combinations thereof. In this embodiment, purge device 140 comprises a tubular housing or body 142 having a central or longitudinal axis 142a, end panels 145 closing off the ends of body 142, and a gas injection port 146 extending radially through body 142. Together, body 142 and end panels 145 define an inner cavity or chamber 144 within device 140. Port 146 is disposed on the lower side of body 142 and provides fluid communication between chamber 144 and the surrounding ambient environment. Thus, any fluid within chamber 144 will be pressurized to the hydrostatic pressure of the ambient water disposed at the location where the radiography is to be conducted. Consequently, body 142 does not need to be able to withstand a relatively large pressure differential between chamber 144 and the surrounding environment. In this embodiment, device 140 is made of aluminum, however, in general, any material suitable for subsea use may be used. A handle 148 is attached to body 142 to facilitate manipulation and positioning of device 140 by a subsea ROV. In this embodiment, handle 148 is disposed on the radially opposite side of body 142 from port 146. Although purge device 140 comprises a rigid tubular body 142 in this embodiment, in other embodiments, the purge device (e.g., purge device 140) comprises a flexible, collapsible structure such as a bladder or ballonet fabricated from a flexible gas and water tight material suitable for subsea use such as an elastomeric material. In still other embodiments, the purge device may be a rectangular structure.

Referring still to FIG. 6, gas supply 150 contains gas for purging internal chamber 144 of water when the radiography is to be carried out. Gas supply 150 includes a tank 151 containing a pressurized gaseous fluid, such as air, a flexible supply conduit 152, and a valve 154 for controlling the flow of gas from supply tank 151, through conduit 152 into chamber 144. In this embodiment, gas supply 150 is mounted to a skid 153 disposed on the sea floor. However, in other embodiments, the gas supply (e.g., gas supply 150) can be mounted to other devices such as a subsea ROV.

Referring still to FIG. 6, use of system 100 will now be explained with respect to its use with imaging cassette 10 previously described herein to radiographically inspect an underwater object of interest. In FIG. 6, the object of interest is a pipe section 180 having a first side 180a and a second side 180b opposite first side 180a (i.e., 180° from first side 180a). In this embodiment, the components of system 100 (e.g., device 140, source holder 120, gas supply 150) are lowered subsea with wireline or ROVs and positioned with ROVs. During subsea deployment, cover 139 is preferably in the closed position to limit and/or prevent exposure of cassette 10 to radiation from source 130. Cassette 10 is positioned along second side 180b of pipe section 180 and held in place by magnet 85 as previously described. With cover 139 locked in the closed position, shuttered radiation source holder 120 and water exclusion device 140 are positioned adjacent first side 180a, generally opposite cassette 10. Holder 120 and device 140 can be held in position by one or more subsea ROVs (not shown). Water exclusion device 140 is generally positioned and oriented such that a projection of central axis 142a intersects cassette 10 and aperture 127. Gas supply 150 is positioned proximal the site of the radiography. In applications where the object of interest is adjacent the sea floor, skid 153 can be placed on the sea floor. Flexible conduit 152 extends from valve 154 to proximal port 146 of device 140. Conduit 152 may held by another ROV manipulating arm or may be clamped to an adjacent structure in a position such that its outlet 155 is disposed immediately below port 146. Thus, when valve 154 is opened, the relatively less dense gas within tank 151 flows upward through conduit 152 into chamber 144, thereby displacing the relatively denser water in chamber 144, which is purged through port 146. Displacing water within chamber 144 with a gas (e.g., air) allows for radiation to be transmitted from source 130 to pipe section 180 substantially unattenuated or unaffected, given that fluids like water have a substantially higher attenuating effect on electromagnetic radiation as compared to a gas, such as air, resulting in relatively long exposure periods.

Once water exclusion device 140 is in position, and water within chamber 144 has been purged, rotatable shutter 134 of the shuttered radiation source holder 120 is unlocked and rotated to the open position shown in FIG. 7. In this position, radiation emitted from source 130 is no longer restricted by cover 139, and thus, allowed to emanate from housing 121, pass through device 140, and expose the phosphor particles of imaging plate 12 in imaging cassette 10 to radiation, leading to the creation (upon later processing) of an image of pipe section 180.

Figure 8:
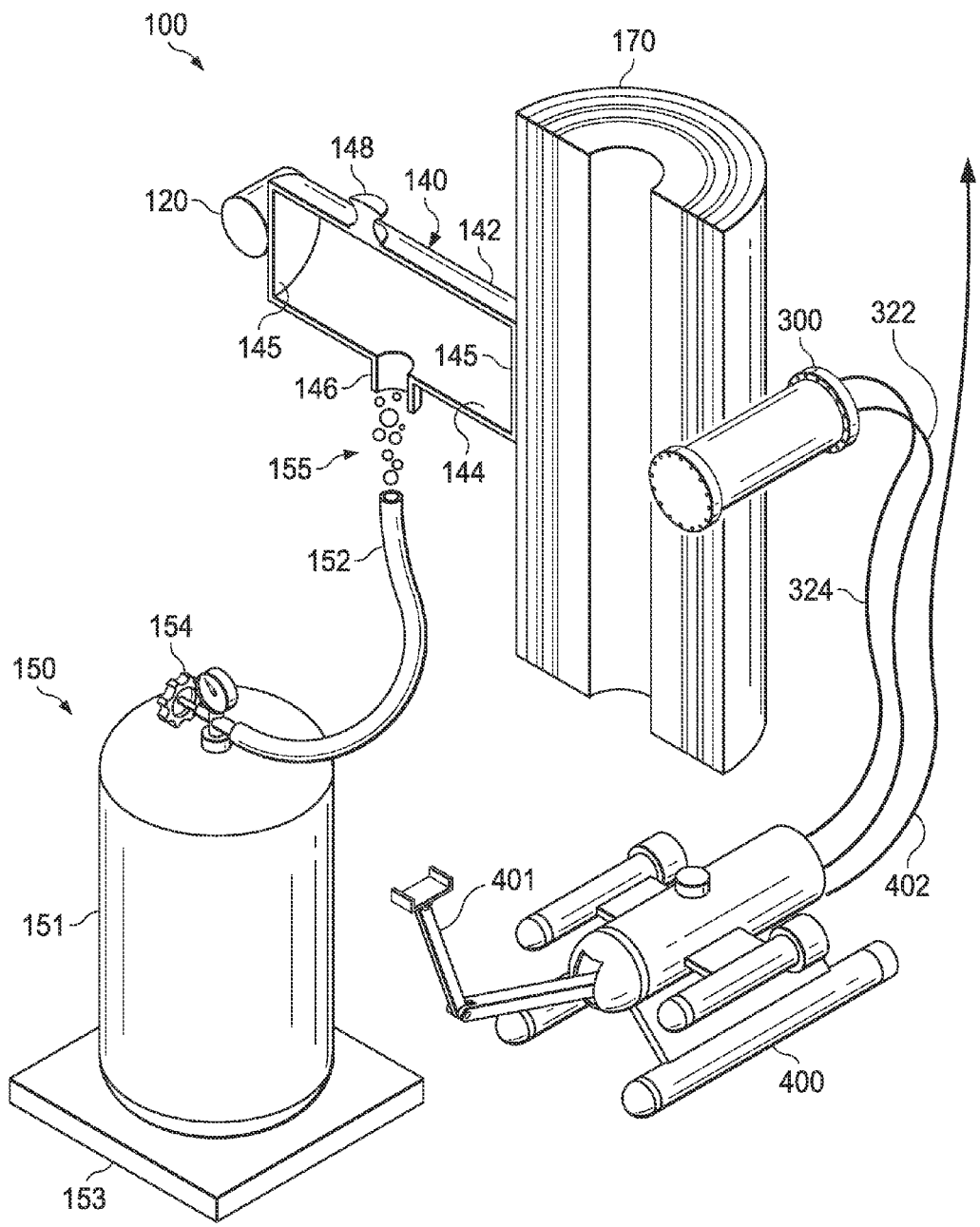
FIG. 8 is a schematic view, partly in cross section, of an embodiment of an underwater radiography system in accordance with the principles described herein.
Figure 9:
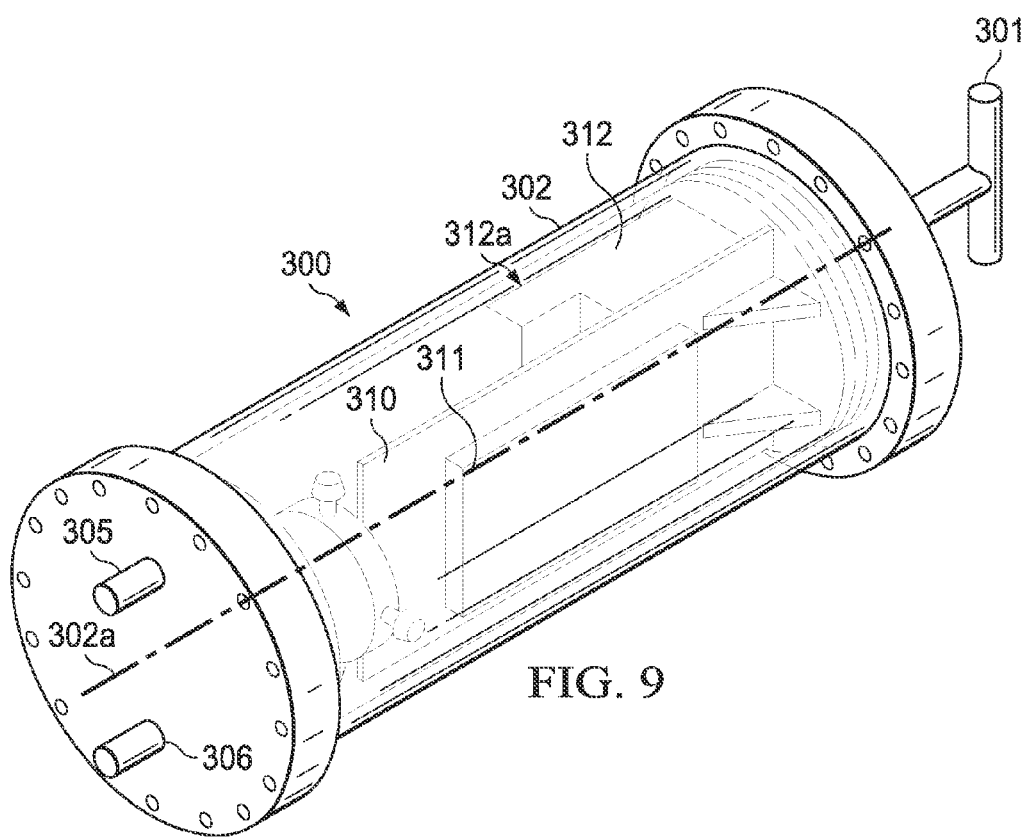
FIG. 9 is a perspective view of an embodiment of an underwater digital radiography receiver in accordance with the principles described herein.

Referring now to FIGS. 8 and 9, another embodiment of a subsea radiography system 200 is shown. System 200 is similar to system 100. Namely, system 200 includes a shuttered radiation source holder 120, a water exclusion device 140, and gas supply 150, each as previously described. However, in this embodiment, system 200 includes a digital radiography receiver 300 in place of cassette 10. Receiver 300 is configured for the continuous creation and transmission of radiographic video images. In this embodiment, receiver 300 generally comprises a water tight pressure vessel 302 having a central or longitudinal axis 302a and that is sufficiently strong to withstand the pressure differential between an internal atmospheric pressure and an external hydrostatic water pressure at a depth of ~5,000 feet. Vessel 302 includes a handle 301 configured to be grasped by the manipulating arm of an ROV, allowing receiver 300 to be manipulated, positioned, and oriented a subsea ROV.

Housing 300 houses at approximately atmospheric pressure digital radiography components configured for creating video images of an underwater object of interest and transmitting those video images to a surface vessel for review and analysis. In particular, pressure vessel 302 houses a support plate or board 310 secured to an end cap of vessel 302, a control, readout, and communication computer 311 secured to plate 310, and an amorphous silicon flat panel detector 312 secured to plate 310. In this embodiment, detector 312 is a PaxScan® 2520D detector as supplied by Varian Medical Systems, Inc. of Palo Alto, Calif. Panel 312 is supported within vessel 302 with an outer detection surface 312a oriented generally parallel to axis 302a and facing radially outwardly with respect to axis 302a. No other components are positioned between the detection surface of panel 312 and the wall of vessel 302. Power is supplied to receiver 300 via power umbilical 322 coupled between a power connector 305 and ROV 400. Similarly, control and data signals are communicated between a control connector 306 of receiver 300 and ROV 400 via control umbilical 324. In turn, power as well as data and control signals are communicated between ROV 400 and a surface vessel (e.g., vessel 80) via ROV umbilical 402. As best shown in FIG. 9, power connector 305 and control connector 306 of receiver 300 each provide a water tight and pressure sealed connection between components internal to vessel 302 and the respective umbilical cables 322, 324.

In use, shuttered radiation source holder 120, water exclusion device 140, and gas supply 150 are deployed and positioned as previously described herein. Using manipulating arm 401, ROV 400 grasps handle 301 and positions digital receiver 300 adjacent pipe section 180 such that panel 312 is intersected by and perpendicular to a projection of axis 142a. Thereafter, gas supply 150 is employed to purge device 140 if water as previously described. In addition, cover 139 is moved to an open position to begin exposing panel 312 to radiation emitted by source 130. Power and control signals are transmitted to receiver 300 via umbilicals 322, 324 to command it to begin its operation of creating and transmitting radiographic video signals. Specifically, radiation received by amorphous silica flat panel detector 312 in receiver 300 is converted to light and the light, in turn, is converted to digital video signals that are transmitted to the surface via control umbilical 324 and ROV umbilical 402. In general, computer 311 offers the potential to increase the transmission rate of image data to the surface, but could be removed from receiver 300 if a slower data transmission rate is acceptable or if a high bandwidth link to the surface is available.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A system for subsea imaging, comprising:
a first plate having an inner surface, an outer surface, and a cavity formed in the inner surface;
a phosphor imaging plate disposed in the cavity;
a second plate having an inner surface facing the inner surface of the first plate and an outer surface facing away from the outer surface of the first plate; and
a seal member disposed between the inner surface of the first plate and the inner surface of the second plate, wherein the seal member extends around the perimeter of the cavity and is configured to seal the phosphor imaging plate and the cavity from intrusion water.

2. The system of claim 1, further comprising at least one intensifying screen disposed in the cavity in engagement with the phosphor imaging plate.

3. The system of claim 2, wherein the imaging plate and the intensifying screen form a stack having a stack height, and wherein the cavity has a depth that is less than the stack height.

4. The system of claim 1, further comprising:
a frame disposed about the first plate and the second plate; and
a plurality of fasteners securing the frame to the first plate and the second plate.

5. The system of claim 4, wherein the frame comprises:
a first frame member disposed about the periphery of the outer surface of the first plate; and
a second frame member disposed about the periphery of the outer surface of the second plate.

6. The system of claim 5, wherein each fastener extends through the first frame member, the second frame member, the first plate and the second plate.

7. The system of claim 5, wherein the first plate and the second plate are compressed together by the frame.

8. The system of claim 5, further comprising at least one magnet coupled to the frame.

9. The system of claim 4, wherein the frame comprises a ferro-magnetic metal.

10. An apparatus for positioning a radiation source underwater for use in nondestructive testing, the apparatus comprising:
a holder;
a radiation source coupled to the holder, wherein the radiation source is configured to emit radiation toward an object of interest; and
at least one magnet coupled to the holder, wherein the magnet is configured to hold the holder in position relative to the object of interest.

11. The apparatus of claim 10, wherein the holder includes a threaded bore that threadedly receives a housing that contains the radiation source.

12. The apparatus of claim 10, wherein the holder includes a handle configured to be grasped by a subsea ROV.

13. The apparatus of claim 10, wherein the holder comprises a base, a pillar extending from the base, and an arm extending perpendicularly from the pillar, wherein the radiation source is coupled to the arm and the magnet is secured to the base.

14. The apparatus of claim 10, wherein the magnet comprises Neodymium-Iron.

15. A method for conducting radiography on a subsea object of interest, the method comprising:
assembling an imaging cassette by compressing a seal member between a pair of support plates to seal an imaging plate between the pair of support plates;
coupling a radiation source to a radiation source holder;
positioning the radiation source holder in a first subsea location relative to the object of interest;
positioning the cassette subsea on the opposite side of the object of interest from the radiation source; and
irradiating the object of interest through the water disposed between the object of interest and the radiation source.

16. The method of claim 15, further comprising retaining the cassette opposite the radiation source in a substantially motionless position for a predetermined duration of time.

17. The method of claim 16, further comprising holding the cassette in position opposite the radiation source with at least one magnet.

18. The method of claim 16 wherein the predetermined duration of time is greater than 20 minutes.

19. The method of claim 15, further comprising transporting the radiation source and the cassette to the object via one or more ROV's.

20. The method of claim 15, farther comprising holding the cassette in position opposite the radiation source with a subsea ROV.

21. The method of claim 15, further comprising attaching the radiation source holder to a metallic underwater support with at least one magnet.

22. The method of claim 21, further comprising holding the cassette opposite the radiation source with at least one magnet.

23. The method of claim 22, wherein each magnet comprises Neodymium-Iron.

24. The method of claim 21, wherein the radiation source holder comprises:
a base;
a pillar extending from the base; and
an arm extending perpendicularly from the pillar, wherein the radiation source is coupled to the arm and the magnet is secured to the base.

25. The method of claim 15, further comprising preventing the intrusion of water into the imaging cassette while irradiating the object of interest.

* * * * *

UNITED STATES PATENT AND TRADEMARK OFFICE
CERTIFICATE OF CORRECTION

| | |
|---|---|
| PATENT NO. | : 8,938,046 B2 |
| APPLICATION NO. | : 13/458260 |
| DATED | : January 20, 2015 |
| INVENTOR(S) | : James Hunter et al. |

It is certified that error appears in the above-identified patent and that said Letters Patent is hereby corrected as shown below:

In the Specification

Column 1, line 13-14, reads "STATEMENT REGARDING FEDERALLY SPONSORED RESEARCH OR DEVELOPMENT"; should read "STATEMENT REGARDING GOVERNMENT RIGHTS"

Signed and Sealed this
Twelfth Day of May, 2015

Michelle K. Lee
*Director of the United States Patent and Trademark Office*